United States Patent [19]

Kallok

[11] Patent Number: 4,727,877

[45] Date of Patent: Mar. 1, 1988

[54] METHOD AND APPARATUS FOR LOW ENERGY ENDOCARDIAL DEFIBRILLATION

[75] Inventor: Michael J. Kallok, New Brighton, Minn.

[73] Assignee: Medtronic, Inc., Minneapolis, Minn.

[21] Appl. No.: 894,753

[22] Filed: Aug. 12, 1986

Related U.S. Application Data

[63] Continuation of Ser. No. 683,298, Dec. 18, 1984, abandoned.

[51] Int. Cl.⁴ .................................................. A61N 1/36
[52] U.S. Cl. .................................................. 128/419 D
[58] Field of Search .................................................. 128/419 D

[56] References Cited

U.S. PATENT DOCUMENTS

| | | | |
|---|---|---|---|
| 4,030,509 | 6/1977 | Heilman et al. | 128/419 D |
| 4,332,259 | 6/1982 | McCorkle, Jr. | 128/786 |
| 4,548,203 | 10/1985 | Tacker | 128/419 D |

FOREIGN PATENT DOCUMENTS

| | | | |
|---|---|---|---|
| 95726 | 12/1983 | European Pat. Off. | 128/419 D |
| 0095726 | 12/1983 | European Pat. Off. | |
| 2853253 | 6/1980 | Fed. Rep. of Germany | |
| 3236756 | 4/1984 | Fed. Rep. of Germany | |
| 2257312 | 1/1974 | France | |

Primary Examiner—William E. Kamm
Attorney, Agent, or Firm—Joseph F. Breimayer; Robert C. Beck; John L. Rooney

[57] ABSTRACT

Ventricular fibrillation and other tachyarrhythmias are controlled by delivery of two sequential impulses to two pairs of electrodes placed partially within or adjacent to the heart. One electrode pair is provided by an endocardial lead which includes a distal electrode adapted to reside in the apex of the right ventricle and a proximal electrode designed to lie in the superior vena cava. The second electrode pair comprises the distal electrode within the right ventricle and a further electrode lodged in or adjacent to the coronary sinus. The metal case of the implantable pulse generator which supplies pulses to the electrode pairs may be substituted for the coronary sinus electrode if the pulse generator is implanted above and to the left of the heart in the left pectoral region of the patient's body. Alternatively, a subcutaneous plate electrode may be substituted for the can, obviating the need for implanting the generator in the left pectoral region. The system also works for temporary use with a skin electrode pair with the catheter in conjunction with an external defibrillator. This disposition of electrode pairs produces a temporal and spatial summation of the delivered energy which results in a reduction in the energy required for defibrillation or cardioversion, and allows the use of less traumatic surgical procedures than epicardial lead systems.

24 Claims, 5 Drawing Figures

METHOD AND APPARATUS FOR LOW ENERGY ENDOCARDIAL DEFIBRILLATION

This is a continuation of co-pending application Ser. No. 683,298 filed on Dec. 18, 1984, now abandoned.

BACKGROUND OF THE INVENTION

1. Field of the Invention

This invention relates to the control of cardiac ventricular tachyarrhythmias, including fibrillation, and more particularly to an improved method and apparatus employing an endocardial implementation technique for ease of implantation.

2. Description of the Prior Art

Ventricular fibrillation is a rapid, uncoordinated and ineffectual arrhythmia of the heart which results in death in a matter of a few minutes after onset unless treated effectively. The most effective therapy is application of an electrical shock of sufficient strength to depolarize most of the ventricular cells. Typically, for the hospitalized patient, the shock is applied by way of a pair of electrodes ("paddles") placed on the chest of the patient. An alternative effective therapy is implantation of an automatic defibrillator designed to detect the onset of fibrillation and to apply the corrective shock to an implanted electrode system.

Research to provide an automatic implantable standby defibrillator has been in progress for over fifteen years, yet the first implantation of such a device has only recently taken place. The very earliest attempts to directly defibrillate the exposed heart employed paddle-style electrodes which simulated the paddle electrodes used in external defibrillators. Because of the ease of implantation, efforts were quickly shifted towards the use of transvenous leads, and much effort was expended in attempting to provide a practical transvenous defibrillator. A suitable transvenous lead which met the requirements of ease of placement and minimization of defibrillation energy thresholds is described in the commonly assigned U.S. Pat. No. 4,355,646. Leads of the type described in this patent have been recently implanted with an automatic low energy cardioverter; however, endocardial leads have not been used chronically in patients with higher energy automatic implantable defibrillators.

Instead the lead systems employed clinically with an automatic implantable standby defibrillator for controlling ventricular fibrillation comprise an epicardial electrode applied to the lower part of the epicardium (the outer wall of the heart) and a second electrode inserted transvenously outside the heart in the superior vena cava (SVC) which is one of the large blood vessels. This lead system is the so-called "apical-SVC electrode system" which is shown in Heilman et al U.S. Pat. No. 4,030,509 and in the medical literature. Basically, it was found by Heilman et al and others working in the area that the energy required for defibrillation was lower using epicardial electrodes than could be obtained using the endocardial electrodes available to Heilman et al. In any event, it was also found necessary to employ the very large surface area electrodes that could be devised by using the epicardial approach because the energy required to defibrillate the average patient in actual clinical use remained relatively high and electrode-tissue current density dictated such large surface area electrodes.

The apical-SVC system contacts the left ventricle which comprises ninety percent of the heart tissue and is therefore efficient in distributing the defibrillating current throughout the ventricles, thereby minimizing to the extent possible the energy required to defibrillate. Unfortunately, major surgery is required to implant the apical electrode on the epicardium. For most candidate patients, such major surgery is not tolerable except as a last resort.

Turning to the stimulation technique, the automatic implantable defibrillators and cardioverters which have been implanted to date clinically employ a single pulse delivered between one set of electrodes on the lead systems previously described. It has been suggested in the past to defibrillate by use of sequential pulses applied to one or more sets of electrode pairs distributed on the epicardium of the heart or on the patient's chest for external use. For example, it has been suggested in the Tacker et al European Patent Application Ser. No. 0 095 726 that cardiac ventricular defibrillation or cardioversion may be treated by delivery of two sequential current pulses to separate pairs of electrodes orthogonally placed around the outside of the heart in the epicardial-pericardial space. It is claimed that this system provides a dramatic reduction in the voltage, current and energy required to defibrillate when compared to the previously described electrode systems. However, the system described by Tacker et al employs epicardial electrodes which must be precisely spaced about the epicardium and fixed in same manner to prevent their subsequent dislocation. Although Tacker et al propose a self-fixing electrode system applied through a limited thoracotomy, it is an open question whether such a system can be realized that will be reliable enough for chronic implantation. Instead, it is expected that a major thoracotomy may be required in order to adequately secure the electrodes in position.

Tacker et al further criticize any use of endocardial lead systems because of perceived problems of fibrosis, blood clots and embolus formations, and the associated risk of stroke and infarction. The system provided by Tacket et al therefore contemplates an entirely epicardial approach.

SUMMARY OF THE INVENTION

The present invention provides a transvenous defibrillation lead system and the delivery of sequential pulses to defibrillate or cardiovert a heart in fibrillation or tachycardia at very low energy levels in comparison to the prior art single pulse defibrillation and cardioversion techniques. More particularly, two pulses are delivered to the ventricles, one pulse in an axial direction of the heart between the apex of the ventricles and the superior vena cava and a further pulse, either before or after the first pulse, in a direction defined by the apex of the ventricles and a region of the heart traversed by the coronary sinus. The interpulse spacing may vary between roughly 0.1 of a millisecond and 10 to 20 milliseconds, but is preferably shorter than 1 millisecond. The sequential application of the two stimulating pulses to the two regions of the heart provide for a spacial summation effect for the defibrillating current resulting a reduction of the voltage, current and energy required to defibrillate when compared to the previously described electrode systems with the possible exception of the system described in the European Patent Application Ser. No. 0 095 726.

Preferably, a single catheter of the type described in the aforementioned U.S. Pat. No. 4,355,646 is employed to provide the first electrode pair comprising an electrode in the apex of the right ventricle and an electrode in the superior vena cava. The second electrode pair is provided by the ventricular tip electrode of the aforementioned lead and a further electrode placed in or adjacent to the coronary sinus, for example, by way of a transvenous superior vena cava right atrial lead. The second electrode of the second pair may be provided by the case of the implantable defibrillator, if appropriately implanted in the subpectoral region on the left side of the chest. Alternatively, the second electrode of the second pair may be a large and different plate electrode placed subcutaneously in the subpectoral region or in the pericardial spaced adjacent to the lateral, should that space be otherwise opened in the course of heart surgery.

In addition, the system of the present invention may be efficaciously employed for temporary stimulation while a patient is in the hospital recovering from heart surgery or an infarction. Under such circumstances of acute cardiac care, the transvenous lead system providing the first electrode pair and the first electrode of the second electrode pair may be employed with a skin patch electrode overlying the left pectoral region of the heart near the apex beat.

Other advantages and features of the invention will be apparent from the following description of the accompanying drawings which illustrate and compare the invention with the prior art and also show preferred embodiments exemplifying the best modes of carrying out the invention as presently perceived.

DETAILED DESCRIPTION OF THE PREFERRED EMBODIMENTS

Figure 1:
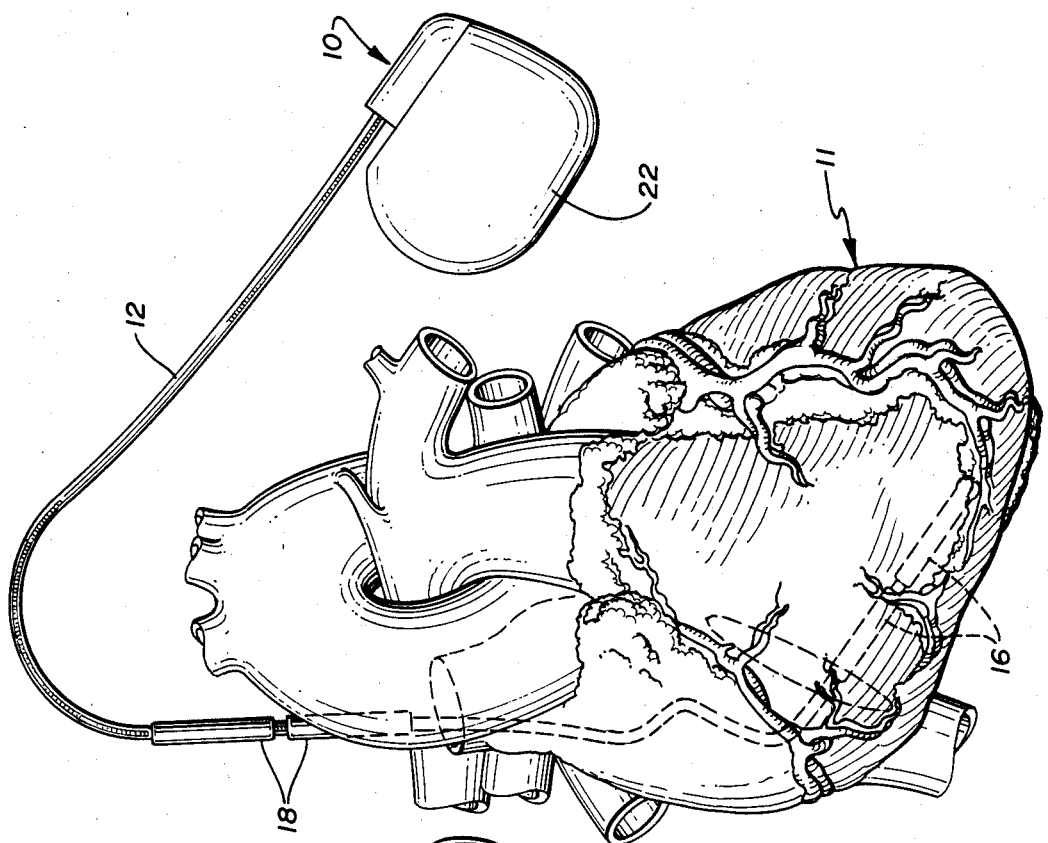
FIG. 1 is a simplified drawing of a cutaway anterior view of the heart showing the arrangement of the pulse generator and leads comprising the system that performs the technique of the present invention in a first embodiment wherein the first electrode pair and second electrode pair are carried entirely by endocardial leads.

The preferred embodiments of the present invention are embodied in a system comprising a pulse generator and two pairs of stimulating electrodes arranged about the heart so that the pulse generator may provide sequential pulse stimulations (SPS) between the two electrode pairs to reduce the effected stimulation energy necessary to defibrillate a heart and terminate fibrillation or to cardiovert a tachycardia. In reference to FIG. 1, the pulse generator 10 is intended to be implanted subcutaneously in the left pectoral region of the body. It will be understood that the pulse generator 10 may comprise the combination of a pacemaker operable in any of the known modes of operation in conjunction with the automatic defibrillator and/or cardioverter of the system of the present invention. Such a pulse generator is described in the aforementioned European Patent Application Ser. No. 0 095 726. But for purposes of simplifying the description, only the operation of the SPS defibrillator shall be described specifically in conjunction with the lead system and technique of the present invention.

The pulse generator 10 is coupled to first and second leads 12 and 14 which are connected to the output circuit of the SPS pulse generator in the conventional manner. The first lead 12 carries the first electrode pair comprising electrodes 16 and 18, and the second lead 14 carries a third electrode 20. The heart 11 is depicted in cutaway to reveal the electrodes 16 and 20 and from the anterior view.

The first lead 12 may correspond to the lead shown in and described in the aforementioned U.S. Pat. No. 4,355,646, and is intended to be implanted in such a way that the first electrode 16 is located within the right ventricle and the second electrode 18 is situated in the superior vena cava. The second lead 14 extends from the pulse generator 10 through the venous system, the superior vena cava, the right atrium and into the coronary sinus. This coronary sinus (CS) lead 14 has an electrode 20, comprising three conductive rings connected in series, at or near its distal tip which is intended to be lodged in the coronary sinus.

The first electrode pair comprises the electrodes 16 and 18 on the first lead 12 and the second electrode pair comprises the electrodes 16 and 20 on the first lead 12 and the seond lead 14 respectively. In operation, it is contemplated that the pulse generator 10 will comprise circuitry capable of emitting a first pulse between the first electrode pair 16, 18 and a second pulse a short time later or earlier than the first pulse between the second electrode pair 16, 20. The location of electrodes is such that the current flow during the discharge of the first pulse is primarily axial within the heart and primarily in the right ventricle and interventricular septum. The second pulse flows somewhat laterally between the right ventricle and the left ventricle of the heart 11. The summation of the current flow generally encompasses a large portion of the bulk of the right and left ventricles of the heart and has been found sufficient to defibrillate the ventricles with considerably lower energy than the energy required to defibrillate employing the single pulse and single first electrode pair 16, 18.

Figure 2:
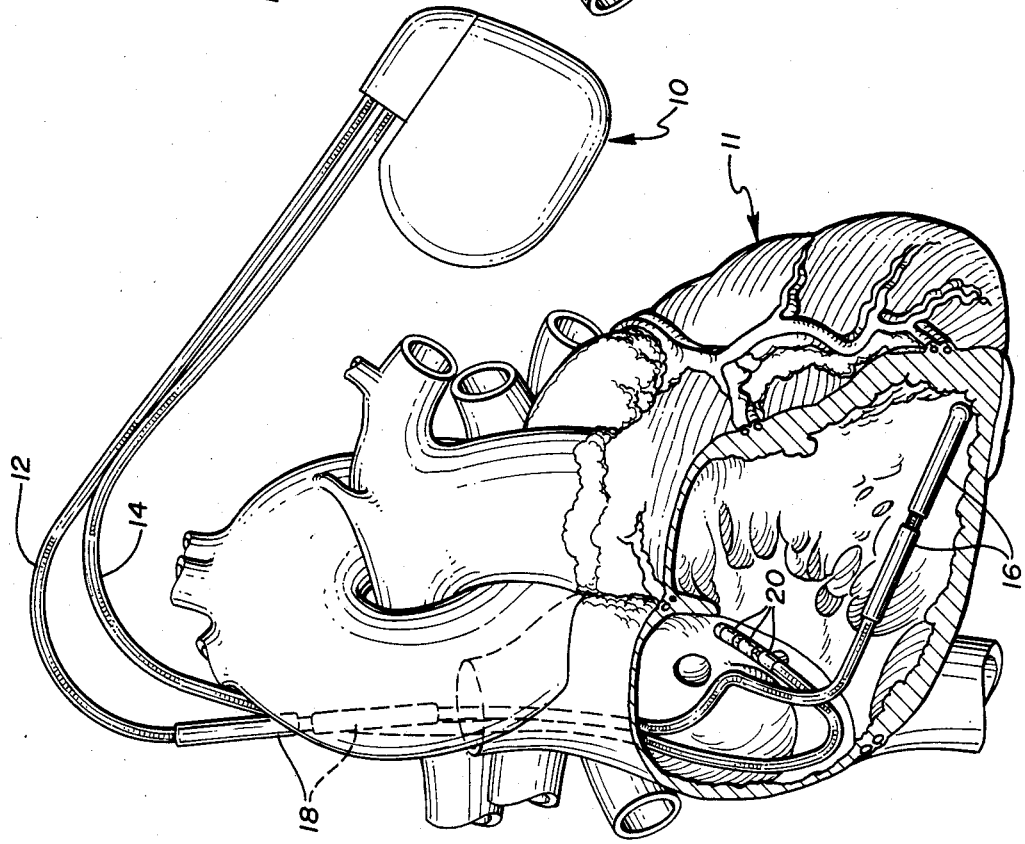
FIG. 2 is a similar anterior view of the heart except that the case of the pulse generator provides the second electrode of the second electrode pair.

Turning now to FIG. 2, a second embodiment of the present invention is shown wherein the external surface or casing 22 of the pulse generator 10 comprises the second electrode of the second electrode pair. In this embodiment, it is contemplated that the pulse generator 10 will be placed in a position lateral to the heart 11 so that the current flow can be achieved across the left ventricle of the heart 11. In operation, a single pulse would be delivered between the first electrode pair 16, 18, and a second impulse would be delivered either before or after the first impulse between the second electrode pair 16, 22.

Figure 3:
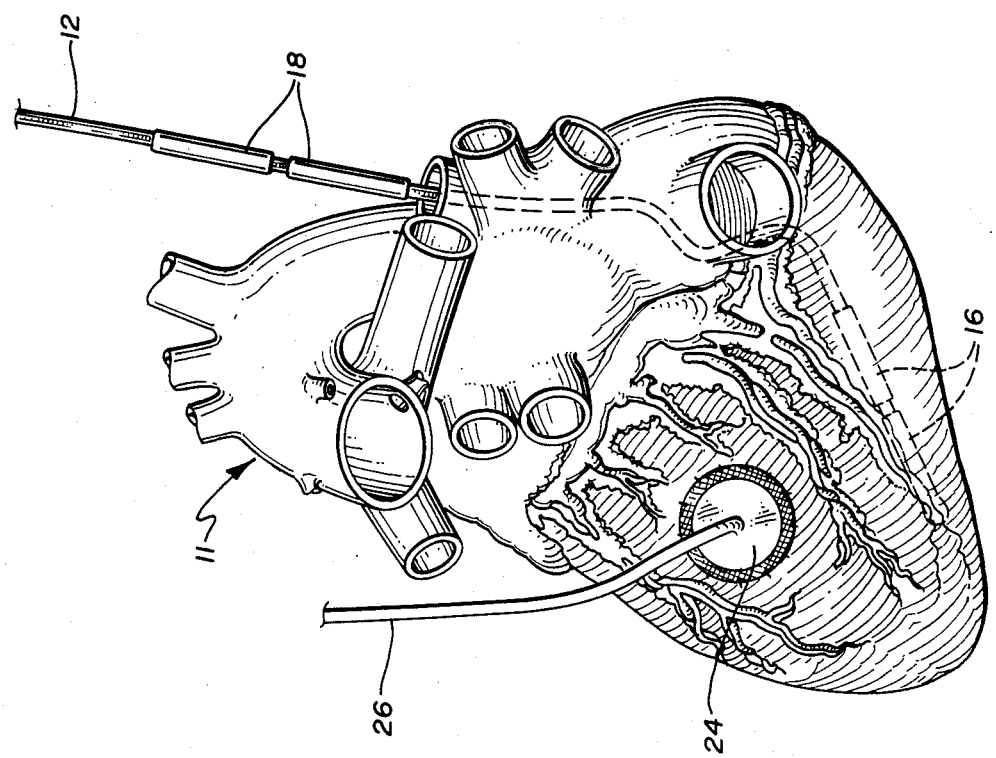
FIG. 3 is a posterior view of the heart wherein a patch electrode is shown providing the second electrode of the second electrode pair.

Turning now to FIG. 3, a third embodiment of the present invention is also depicted wherein the first lead 12 and the first electrode pair 16, 18 is connected to the pulse generator 10 (not shown). The heart 11 is shown in the posterior view. In this embodiment, the second electrode 24 of the second electrode pair 16, 24 it may be attached directly to the epicardium of the heart 11 in proximity to the coronary sinus and connected by a lead 26 to a further terminal of the pulse generator 10 in the manner shown, for example, in FIG. 1. This embodiment may be employed in the situation where the heart 11 is exposed during surgery for other reasons. Although the electrode 24 is shown sutured to the epicardium of the heart 11, a large surface area plate electrode could as well be employed in the region inside the body cavity but outside the pericardium, preferably outside the thoracic cavity in a subcutaneous or submuscular region of the left anterior chest wall.

Figure 4:
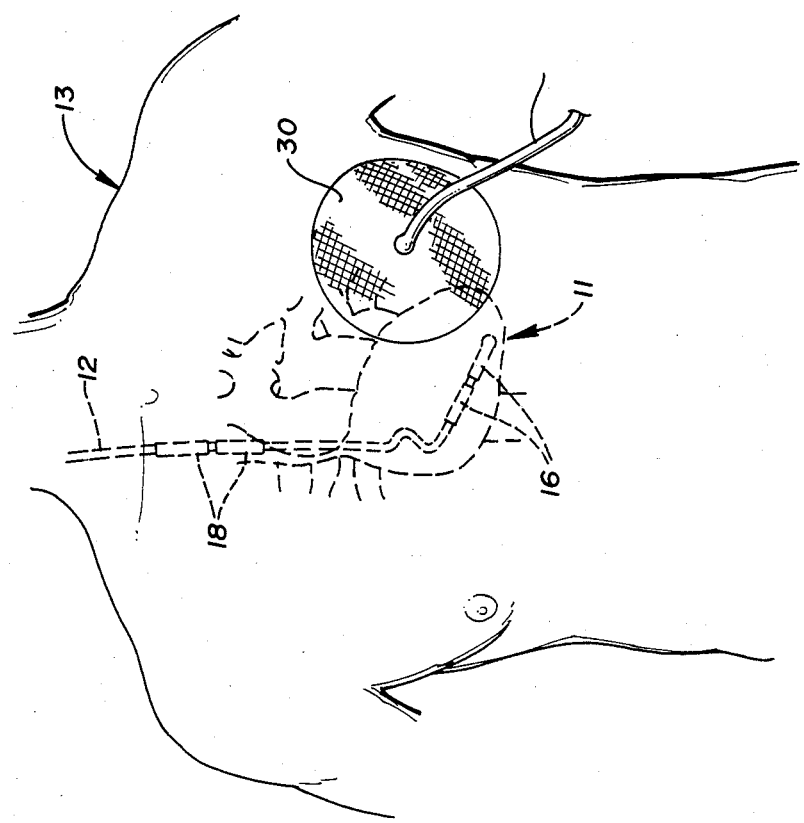
FIG. 4 is an anterior view of the torso with the heart wherein it is contemplated that the system and technique of FIG. 4 shall be used for temporary automatic standby external defibrillation by means of an external pulse generator (not shown)

Referring now to FIG. 4, an electrode system for effecting temporary, in-hospital cardioversion or defibrillation is shown in relation to an anterior view of a human torso 13. In this embodiment, it is contemplated that the lead system will include the first lead 12 transvenously inserted into the right ventricle of the patient's heart 11 so that the first electrode pair 16, 18 is positioned in the manner previously described. The second electrode pair constitutes the electrode 16 and a large surface skin electrode 30 placed over the patient's left ventricle and on the skin in the left pectoral region of the patient's body. The second electrode pair 16, 30 thus accomplishes the function of the second electrode pairs previously described in an acute or temporary mode of operation of the system. In this embodiment, it is contemplated that the pulse generator would be coupled to the first lead 14 and the second lead 32 to provide the first and second pulses of the sequential pulse system in the manner previously described, although the pulse generator of course would not be implanted.

The embodiments of FIGS. 1-3 contemplate an automatic detection of either a tachycardia condition or fibrillation in order to trigger the charging of a capacitive discharge circuit. After a time delay to complete the charging process, the circuit would be readied to deliver the first and second capacitive discharge impulses to the first and second electrode pairs in sequence. It is contemplated that in the event that heart rhythm spontaneously recovers during the charging process or within a waiting time interval after the charging process is complete that the system would be reset to a standby condition to await the re-emergence of tachycardia or fibrillation.

The sequential pulse system used in the technique and apparatus of the present invention reduces the current required for cardioversion or defibrillation and therefore reduces the power drain on the battery employed in the pulse generator 10 which, in turn, can be reduced in size.

In actual animal and human tests of the various lead systems of FIGS. 1-4, it has been established that the sequential pulse stimulation employing these electrode systems provides markedly lower defibrillation thresholds than the single pulse technique employing a single electrode pair. The graph depicted in FIG. 5 shows the comparative data of animal and human tests (to the extent that human tests are available to date).

Figure 5:
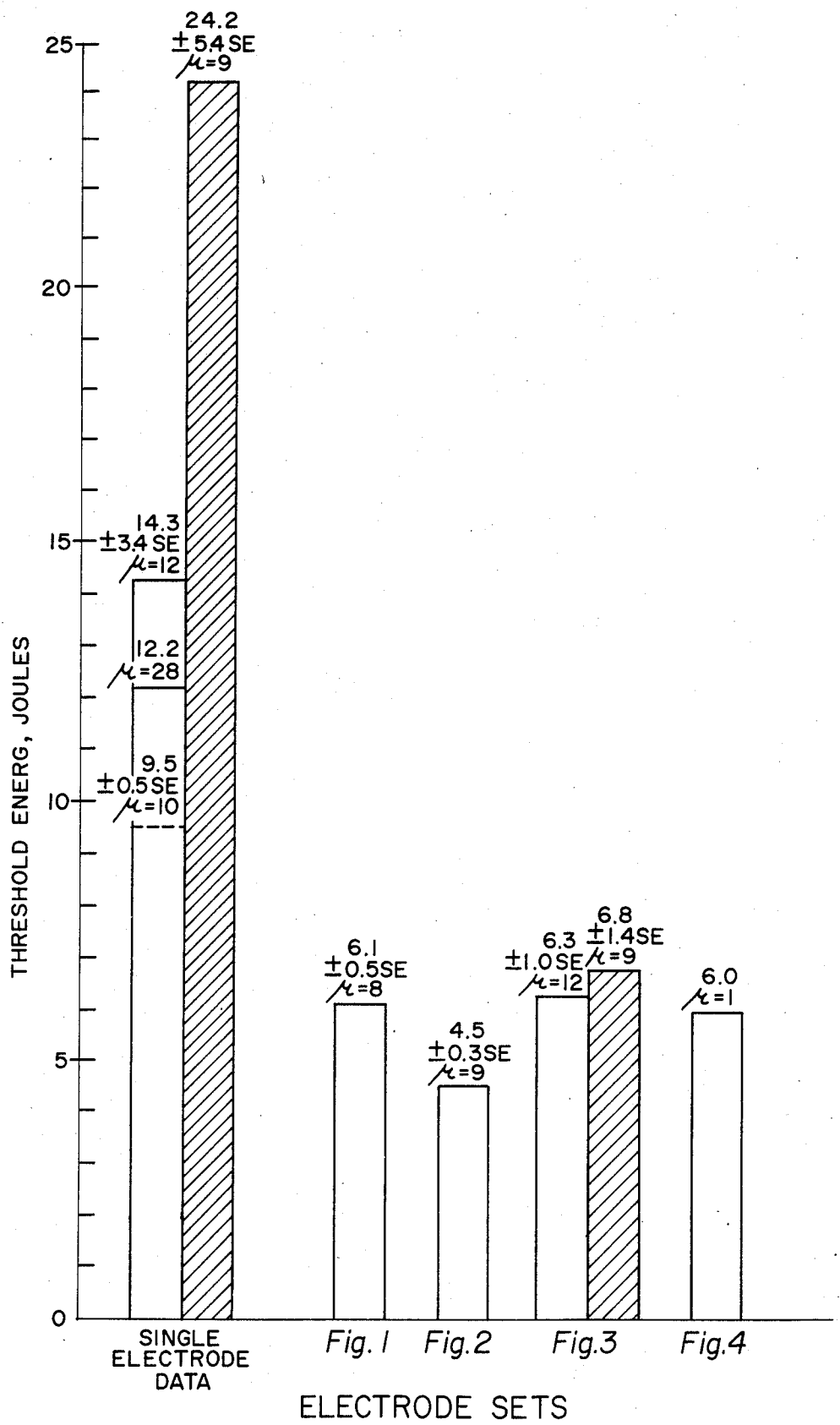
FIG. 5 is a graphical depiction of the relative energies necessary to effect defibrillation as between the embodiments depicted in FIGS. 1–4 in the prior art endocardial defibrillation system.

The bar graph of FIG. 5 shows the mean threshold comparisons of human subjects (lived bar) and dogs (blank bar). The number of subjects (n=) are shown within the bar and the mean thresholds for the number tested are stated in joules and displayed against the threshold energy scale. At the left, the mean defibrillation thresholds are depicted employing a single lead having a first electrode pair only and of the type shown in U.S. Pat. No. 4,355,646 and a single pulse. The four other bars depict thresholds employing sequential pulses and the first and second electrode pairs of FIGS. 1-4. The animal results were obtained in tests of the same population of dogs, although not all dogs had all of the lead systems tested (which accounts for the different values of n). The single pulse technique was used in all animal tests since the first lead 12 was implanted in and available for every test. The animals were fibrillated with 60 Hz current, and defibrillation was attempted 20 seconds later. Values above the bars are mean thresholds for the number of dogs tested. Analysis of variances showed that the mean thresholds obtained with the sequential pulse systems of FIGS. 1-3 all significantly lower than the mean thresholds of the single pulse technique. The FIG. 4 threshold only represents a single animal, which is statistically insignificant alone but its value of 6 joules is comparable to those obtained with the FIGS. 1-3 sequential pulse techniques.

The known clinical evaluation has been limited to tests in the same individual with the single pulse technique and the FIG. 3 sequential pulse technique. The patients' hearts were fibrillated with 60 Hz current and defibrillation was accomplished 10 seconds later. The means values of the thresholds are significantly lower for the sequential pulse technique.

In general, it has been found that the sequential electrical pulses can each have a magnitude of between about 100 and 500 volts for a duration or pulse width of between about 2 and about 8 ms, the pulses being separated by an interval about 0.1 ms to about 2 ms with 0.2 ms being optimal for humans. Of course, it is not necessary that the values be identical and some variation may prove beneficial. Nor does the pulsing sequence appear to make any difference, although test results shown herein were accomplished by first pulsing the first electrode pair and then the second electrode pair after a delay interval of about 1 ms for animals and 0.2 ms for humans in each case.

Based on this preliminary data, it is believed that the sequential pulse stimulation technique employing the first and second electrode pairs as shown herein offers significantly better results than the single pulse stimulation technique with the single lead 12. It is also a significant advantage that the fully implanted system can be accomplished through use of an indwelling coronary sinus electrode or the case of the pulse generator which diminishes the complications of the Purdue Research Foundation epicardial approach described earlier herein. The advantages of this technique can also be realized in cases where the heart is already exposed and an epicardial electrode can be located in the region of the coronary sinus or in emergencies employing the chest skin electrode as described herein.

What is claimed is:

1. A method for controlling cardiac ventricular fibrillation or other tachyarrhythmias by passing an electric current through the heart which comprises:
   disposing a first electrode pair along the longitudinal axis of the heart;
   disposing a second electrode pair laterally between the ventricle and the region of the coronary sinus of the heart; and
   sequentially pulsing each of said electrode pairs at a voltage or voltages providing a temporal and spatial summation of delivered current above the threshold level sufficient to effect defibrillation or cardioversion of the heart.

2. The method of claim 1 wherein said pulses are separated by an interval of at least about 0.1 ms.

3. The method of claim 1 wherein said pulses are separated by an interval of about 0.1 ms to about 2 ms.

4. The method of claims 1, 2 or 3 wherein said pulses have a duration of about 2 ms to about 8 ms.

5. The method of claim 1 wherein the sequential pulsing step comprises subjecting each of said pairs of electrodes in sequence to an electrical pulse at a voltage between about 100 and about 500 volts for a duration between about 2 and about 8 ms, the pulses being separated by an interval of about 0.1 ms to about 2 ms.

6. A method for controlling cardiac ventricular fibrillation or other tachyarrhythmias by passing an electric current through the heart which comprises:
 disposing a first electrode in the right ventricle of the heart;
 disposing a second electrode in the region of the superior vena cava;
 disposing a third electrode in the region of the coronary sinus of the heart; and
 sequentially applying pulses between said first and second electrodes and said first and third electrodes at a voltage or voltages providing a temporal and spatial summation of delivered current above the threshold level sufficient to effect defibrillation or cardioversion of the heart.

7. The method of claim 6 wherein said pulses are separated by an interval of at least about 0.1 ms.

8. The method of claim 6 wherein said pulses are separated by an interval of about 0.1 ms to about 2 ms.

9. The method of claims 6, 7 or 8 wherein said pulses have a duration of about 2 ms to about 8 ms.

10. The method of claim 6 wherein the sequential pulsing step comprises subjecting each of said pairs of electrodes in sequence to an electrical pulse at a voltage between about 100 and about 500 volts for a duration between about 2 and about 8 ms, the pulses being separated by an interval of about 0.1 ms to about 2 ms.

11. The method of claim 6 wherein the step of disposing a third electrode in the region of the coronary sinus further comprises:
 disposing said third electrode through the venous system and into the lumen of the coronary sinus.

12. The method of claim 6 wherein the step of disposing a third electrode in the region of the coronary sinus further comprises:
 disposing said third electrode epicardially alongside the coronary sinus.

13. The method of claim 6 wherein the step of disposing a third electrode in the region of the coronary sinus further comprises:
 disposing said third electrode subcutaneously in the left pectoral region of the body.

14. The method of claim 6 wherein the step of disposing a third electrode in the region of the coronary sinus further comprises:
 disposing said third electrode on the surface of the body overlying the left pectoral region.

15. Apparatus for controlling cardiac ventricular fibrillation or other tachyarrhythmias by passing an electrical current through the heart which comprises:
 means disposing a first pair of electrodes axially along the heart between the atrium and ventricle;
 means disposing a second pair of electrodes between the ventricle and the region of the coronary sinus; and
 means for sequentially pulsing each of said pairs of electrodes at a voltage or voltages providing a temporal and spatial summation of the delivered current above the threshold level sufficient to effect defibrillation or cardioversion of the heart.

16. The apparatus of claim 15 wherein said pulses are separated by an interval of at least about 0.1 ms.

17. The apparatus of claim 15 wherein said pulses are separated by an interval of about 0.1 ms to about 2 ms.

18. The apparatus of claim 15, 16 or 17 wherein each of said pulses has a duration of about 2 ms to about 8 ms.

19. The apparatus of claim 15 wherein the sequential pulsing means comprises means for subjecting each of said pairs of electrodes in sequence to an electrical pulse at a voltage between about 100 and about 500 volts for a duration between about 2 and about 8 ms, the pulses being separated by an interval of about 0.1 ms to about 2 ms.

20. The apparatus of claim 15 or 19 wherein;
 said means disposing said first pair of electrodes further disposes a first electrode in the right ventricle of the heart and a second electrode in the region of the superior vena cava; and
 wherein said second pair of electrodes disposed between the right ventricle and the region of the coronary sinus further comprises the first electrode of the first electrode pair and means disposing a third electrode in the region of the coronary sinus.

21. The apparatus of claim 20 further comprising means for disposing said third electrode transvenously into the lumen of the coronary sinus.

22. The apparatus of claim 21 further comprising means for disposing said third electrode epicardially adjacent to the coronary sinus.

23. The apparatus of claim 21 further comprising means for disposing said third electrode subcutaneously in the left pectoral region of the heart.

24. The apparatus of claim 21 further comprising means for disposing said third electrode on the surface of the body overlying the left pectoral region.

* * * * *